(12) United States Patent
Yokouchi

(10) Patent No.: US 9,714,850 B2
(45) Date of Patent: Jul. 25, 2017

(54) INFORMATION PROCESSING DEVICE AND INFORMATION PROCESSING METHOD

(71) Applicant: JEOL Ltd., Tokyo (JP)

(72) Inventor: Kazushiro Yokouchi, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/875,764

(22) Filed: Oct. 6, 2015

(65) Prior Publication Data

US 2016/0097659 A1    Apr. 7, 2016

(30) Foreign Application Priority Data

Oct. 6, 2014    (JP) .................................. 2014-205615

(51) Int. Cl.
  *G01D 9/00*    (2006.01)
  *G01N 23/227*    (2006.01)
  *G01N 35/00*    (2006.01)

(52) U.S. Cl.
  CPC ......... *G01D 9/005* (2013.01); *G01N 23/2273* (2013.01); *G01N 23/2276* (2013.01); *G01N 35/00722* (2013.01); *G01N 2035/0091* (2013.01); *G01N 2035/00891* (2013.01)

(58) Field of Classification Search
  USPC ........................................................ 250/305
  See application file for complete search history.

(56) References Cited

U.S. PATENT DOCUMENTS

| 8,748,816 B2 * | 6/2014 | Kooijman | .......... G01N 23/2206 250/305 |
| 2003/0026388 A1 | 2/2003 | Numata et al. | |
| 2007/0179715 A1 | 8/2007 | Ariyoshi | |
| 2009/0132858 A1 | 5/2009 | Koeda et al. | |
| 2010/0101339 A1 | 4/2010 | Tatsutani et al. | |
| 2011/0039349 A1 | 2/2011 | Hamada et al. | |
| 2012/0109529 A1 | 5/2012 | Ariyoshi | |
| 2013/0112893 A1 | 5/2013 | Miyake et al. | |

FOREIGN PATENT DOCUMENTS

JP            200820386 A    1/2008

OTHER PUBLICATIONS

Exended European Search Report re EP 15188251.1 dated Feb. 26, 2016.

* cited by examiner

*Primary Examiner* — Nicole Ippolito
*Assistant Examiner* — Hanway Chang
(74) *Attorney, Agent, or Firm* — The Webb Law Firm

(57) ABSTRACT

An information processing device includes a storage section 50 that stores a history relating to the acquisition of measurement data, a history relating to an analysis position within an analyzer, and a history relating to a predetermined operation performed on a specimen using the analyzer as log information linked to time information, and a display control section 22 that performs a control process that displays these histories within a log display area on a display screen 40 in time series based on the log information, the display control section 22 performing a control process that displays a measurement result image generated based on the measurement data on the display screen, and, when an operation input that selects one measurement result image, performing a control process that displays a history that corresponds to the measurement data used to generate the selected measurement result image.

3 Claims, 7 Drawing Sheets

FIG.3

| ID | TIME | HISTORY | MEASUREMENT DATA |
|---|---|---|---|
| 001 | 06:50 | LOADING OF SPECIMEN | – |
| 002 | 07:24 | MOVEMENT OF STAGE | – |
| 003 | 12:03 | ACQUISITION OF MEASUREMENT DATA | data001 |
| 004 | 13:18 | ACQUISITION OF MEASUREMENT DATA | data002 |
| 005 | 13:19 | ACQUISITION OF MEASUREMENT DATA | data003 |
| 006 | 13:20 | ACQUISITION OF MEASUREMENT DATA | data004 |
| 007 | 13:22 | ACQUISITION OF MEASUREMENT DATA | data005 |
| 008 | 13:33 | ACQUISITION OF MEASUREMENT DATA | data006 |
| 009 | 13:55 | ETCHING (30017nm) | – |
| 010 | 14:25 | START OF NEUTRALIZATION | – |
| 011 | 14:38 | ACQUISITION OF MEASUREMENT DATA | data007 |
| 012 | 15:25 | TERMINATION OF NEUTRALIZATION | – |
| 013 | 16:04 | ACQUISITION OF MEASUREMENT DATA | data008 |
| 014 | 16:04 | ACQUISITION OF MEASUREMENT DATA | data008_Al |
| 015 | 16:04 | ACQUISITION OF MEASUREMENT DATA | data008_F |
| 016 | 16:04 | ACQUISITION OF MEASUREMENT DATA | data008_Fe |

FIG.6

```
                                    LI
  ┌─────────────────────────────┐
  │ 06:50  ◆    IN              │
  │ 07:24  ●    FIELD OF VIEW 1 │
  │ 12:03  ◊  [■]  data11       │
  │ 13:18  ◊  [ ]  data12       │
  │ 13:19  ◊  [■]  data13       │
  │ 13:25  ✦       100[nm]      │
  │ 13:33  ◊  [■]  data14       │
  │ 13:47  ◊  [ ]  data15       │
  │ 13:52  ◊  [■]  data16       │
  │ 14:25  ✦       500[nm]      │
  │ 14:41  ◊  [■]  data17       │
  │ 14:50  ◊  [ ]  data18       │
  │ 14:54  ◊  [■]  data19       │
  │ 15:25  ●    FIELD OF VIEW 2 │
  │ 15:33  ◊  [■]  data21       │
  │ 15:36  ◊  [ ]  data22       │
  │ 15:41  ◊  [■]  data23       │
  │ 16:04  ✦       100[nm]      │
  │ 16:16  ◊  [■]  data24       │
  │ 16:18  ◊  [ ]  data25       │
  │ 16:27  ◊  [■]  data26       │
  │ 16:30  ✦       500[nm]      │
  │ 16:32  ◊  [■]  data27       │
  │ 16:44  ◊  [ ]  data28       │
  │ 16:50  ◊  [■]  data29       │
  └─────────────────────────────┘
```

INFORMATION PROCESSING DEVICE AND INFORMATION PROCESSING METHOD

Japanese Patent Application No. 2014-205615 filed on Oct. 6, 2014, is hereby incorporated by reference in its entirety.

BACKGROUND OF THE INVENTION

The present invention relates to an information processing device and a data processing method that process measurement data acquired by an analyzer.

An analyzer such as an Auger electron spectroscope (AES) is used in the field of specimen (sample) analysis in order to analyze the elements present on the surface of a specimen (e.g., JP-A-2008-20386).

The state of the specimen (analysis target) that is analyzed using the analyzer changes with the passage of time due to electron beam irradiation, a surface treatment, and the like that are performed after the specimen has been loaded into the analyzer. In particular, when using an AES or an X-ray photoelectron spectroscope (XPS), the depth profile may be measured while etching the specimen, and depth profile analysis may then be performed. Therefore, it is useful for the user (or the manager or the client) to understand the situation before and after the measurement data was acquired when referring to the measurement data measured (acquired) by the analyzer.

SUMMARY

Several aspects of the invention may provide an information processing device and an information processing method that make it possible to easily understand the situation before and after measurement data was acquired.

According to a first aspect of the invention, there is provided an information processing device that processes measurement data acquired by an analyzer, the information processing device including:

a storage section that stores a history relating to acquisition of the measurement data, a history relating to an analysis position within the analyzer, and a history relating to a predetermined operation performed on a specimen using the analyzer as log information linked to time information; and a display control section that performs a control process that displays the history relating to the acquisition of the measurement data, the history relating to the analysis position, and the history relating to the predetermined operation within a log display area on a display screen in time series based on the log information, the display control section performing a control process that displays a measurement result image generated based on the measurement data on the display screen, and, when an operation input that selects one measurement result image among a plurality of the measurement result images has been performed, performing a control process that displays a history that corresponds to the measurement data used to generate the selected measurement result image within the log display area so as to be specified.

According to a second aspect of the invention, there is provided an information processing method that processes measurement data acquired by an analyzer, the information processing method including:

a storing step that stores a history relating to acquisition of the measurement data, a history relating to an analysis position within the analyzer, and a history relating to a predetermined operation performed on a specimen using the analyzer in a storage section as log information linked to time information; and a display control step that performs a control process that displays the history relating to the acquisition of the measurement data, the history relating to the analysis position, and the history relating to the predetermined operation within a log display area on a display screen in time series based on the log information, the display control step performing a control process that displays a measurement result image generated based on the measurement data on the display screen, and, when an operation input that selects one measurement result image among a plurality of the measurement result images has been performed, performing a control process that displays a history that corresponds to the measurement data used to generate the selected measurement result image within the log display area so as to be specified.

BRIEF DESCRIPTION OF THE SEVERAL VIEWS OF THE DRAWING

FIG. 3 is a table illustrating an example of log information.

FIG. 6 illustrates an example of a log display area.

Figure 1:
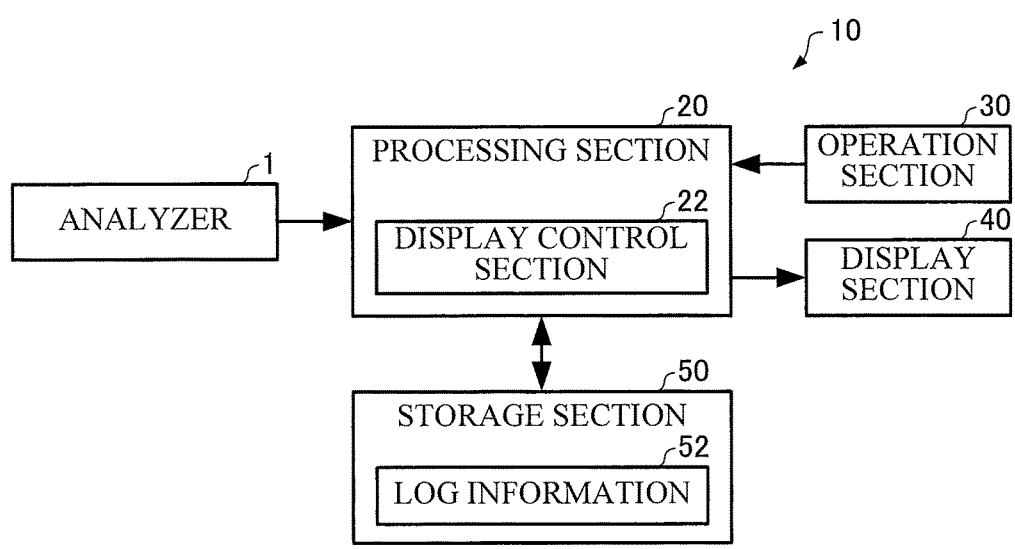
FIG. 1 is a functional block diagram illustrating an example of an information processing device according to one embodiment of the invention.

DETAILED DESCRIPTION OF THE EMBODIMENT (1) According to one embodiment of the invention, an information processing device processes measurement data acquired by an analyzer, the information processing device including:

a storage section that stores a history relating to acquisition of the measurement data, a history relating to an analysis position within the analyzer, and a history relating to a predetermined operation performed on a specimen using the analyzer as log information linked to time information; and a display control section that performs a control process that displays the history relating to the acquisition of the measurement data, the history relating to the analysis position, and the history relating to the predetermined operation within a log display area on a display screen in time series based on the log information, the display control section performing a control process that displays a measurement result image generated based on the measurement data on the display screen, and, when an operation input that selects one measurement result image among a plurality of the measurement result images has been performed, performing a control process that displays a history that corresponds to the measurement data used to generate the selected measurement result image within the log display area so as to be specified.

According to another embodiment of the invention, an information processing method processes measurement data acquired by an analyzer, the information processing method including:

a storing step that stores a history relating to acquisition of the measurement data, a history relating to an analysis position within the analyzer, and a history relating to a predetermined operation performed on a specimen using the analyzer in a storage section as log information linked to time information; and a display control step that performs a control process that displays the history relating to the acquisition of the measurement data, the history relating to the analysis position, and the history relating to the predetermined operation within a log display area on a display screen in time series based on the log information, the display control step performing a control process that displays a measurement result image generated based on the measurement data on the display screen, and, when an operation input that selects one measurement result image among a plurality of the measurement result images has been performed, performing a control process that displays a history that corresponds to the measurement data used to generate the selected measurement result image within the log display area so as to be specified.

According to the above embodiments, since the history relating to the acquisition of the measurement data, the history relating to the analysis position, and the history relating to the predetermined operation performed on the specimen are displayed within the log display area on the display screen in time series, and a history that corresponds to the measurement data used to generate the measurement result image selected by the user is displayed within the log display area so as to be specified, this embodiment makes it possible for the user to easily understand the situation (i.e., the analysis position or the state of the specimen) before and after the measurement data used to generate the measurement result image selected by the user was acquired, and also makes it possible to provide information useful for the user and the like.

(2) In the above information processing device, the display control section may perform a control process that sorts the history relating to the acquisition of the measurement data by the analysis position or the type of the predetermined operation based on the log information, and displays the sorted history. In the information processing method, the display control step may perform a control process that sorts the history relating to the acquisition of the measurement data by the analysis position or the type of the predetermined operation based on the log information, and displays the sorted history.

According to this configuration, since the history relating to the acquisition of the measurement data is sorted by the analysis position or the type of the operation, and the sorted history is displayed, it becomes possible for the user to easily understand the analysis position when each piece of measurement data was acquired, and the state of the specimen when each piece of measurement data was acquired, and also it becomes possible to provide information useful for the user and the like.

Exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. Configuration

FIG. 1 illustrates an example of an information processing device according to one embodiment of the invention. Note that the information processing device may have a configuration in which some of the elements (sections) illustrated in FIG. 1 are omitted.

An information processing device 10 is a device that processes measurement data measured (acquired) by an analyzer 1. An example in which the analyzer 1 is an Auger electron spectroscope (i.e., a scanning electron microscope that includes an Auger electron spectrometer) is described below. Note that the invention may also be applied to a case where the analyzer 1 is an electron probe microanalyzer (EPMA), an X-ray photoelectron spectroscope (XPS or ESCA), or the like.

The information processing device 10 acquires spectral data, elemental map (Auger image) data, secondary electron image (SEM image) data, depth profile (i.e., the concentration distribution in the depth direction) data, and line profile data as the measurement data measured by the analyzer 1. The information processing device 10 includes a processing section 20, an operation section 30, a display section 40, and a storage section 50.

The operation section 30 allows the user to input operation information, and outputs the input operation information to the processing section 20. The function of the operation section 30 may be implemented by hardware such as a keyboard, a mouse, a button, a touch panel, or a touch pad.

The display section 40 displays an image generated by the processing section 20. The function of the display section 40 may be implemented by an LCD, a CRT, a touch panel (that also functions as the operation section 30), or the like.

The storage section 50 stores a program that causes a computer to function as each section of the processing section 20, as well as various types of data, and serves as a work area for the processing section 20. The function of the storage section 50 may be implemented by a hard disk, a RAM, or the like.

Especially, the storage section 50 in this embodiment stores a history relating to the acquisition of the measurement data, a history relating to the analysis position (i.e., the measurement position or the position of the specimen stage) within the analyzer 1, and a history relating to a predetermined operation performed on the specimen using the analyzer 1 (i.e., behavioral record relating to an analytical operation performed by the user) as log information 52 linked to time information. Note that the term "predetermined operation" used herein refers to an operation that can change the state of the specimen. For example, the term "predetermined operation" used herein refers to an operation that effects etching (sputtering) by applying ion beams to the specimen, and the like. The storage section 50 also stores the measurement data measured by the analyzer 1, and a measurement result image generated from the measurement data.

The processing section 20 (computer) performs a process that implements data processing on the measurement data, a process that displays the data processing results on the display screen of the display section 40, and the like. The processing section 20 performs data processing (e.g., smoothing process, differential process, arithmetic operation process, and image synthesis (blending) process) on the measurement data. The function of the processing section 20 may be implemented by hardware such as a processor (e.g., CPU or DSP), or a program. The processing section 20 includes a display control section 22.

The display control section 22 performs a control process that displays the history relating to the acquisition of the measurement data, the history relating to the analysis position, and the history relating to the predetermined operation within a log display area on the display screen in time series based on the log information 52.

The display control section 22 also performs a control process that displays the measurement result image (i.e., an image that visually represents the measurement data) generated based on the measurement data stored in the storage section 50 on the display screen. When an operation input that selects one measurement result image among a plurality of measurement result images has been performed using the operation section 30, the display control section 22 performs a control process that displays a history that corresponds to the measurement data used to generate the selected measurement result image within the log display area so as to be specified (e.g., highlights the history that corresponds to the measurement data).

The display control section 22 may perform a control process that sorts the history relating to the acquisition of the measurement data by the analysis position or the type of the predetermined operation based on the log information 52, and displays the sorted history. The history relating to the acquisition of the measurement data is sorted by tracing the history according to the time information included in the log information 52.

2. Method

A method according to one embodiment of the invention is described below with reference to the drawings.

Figure 2:
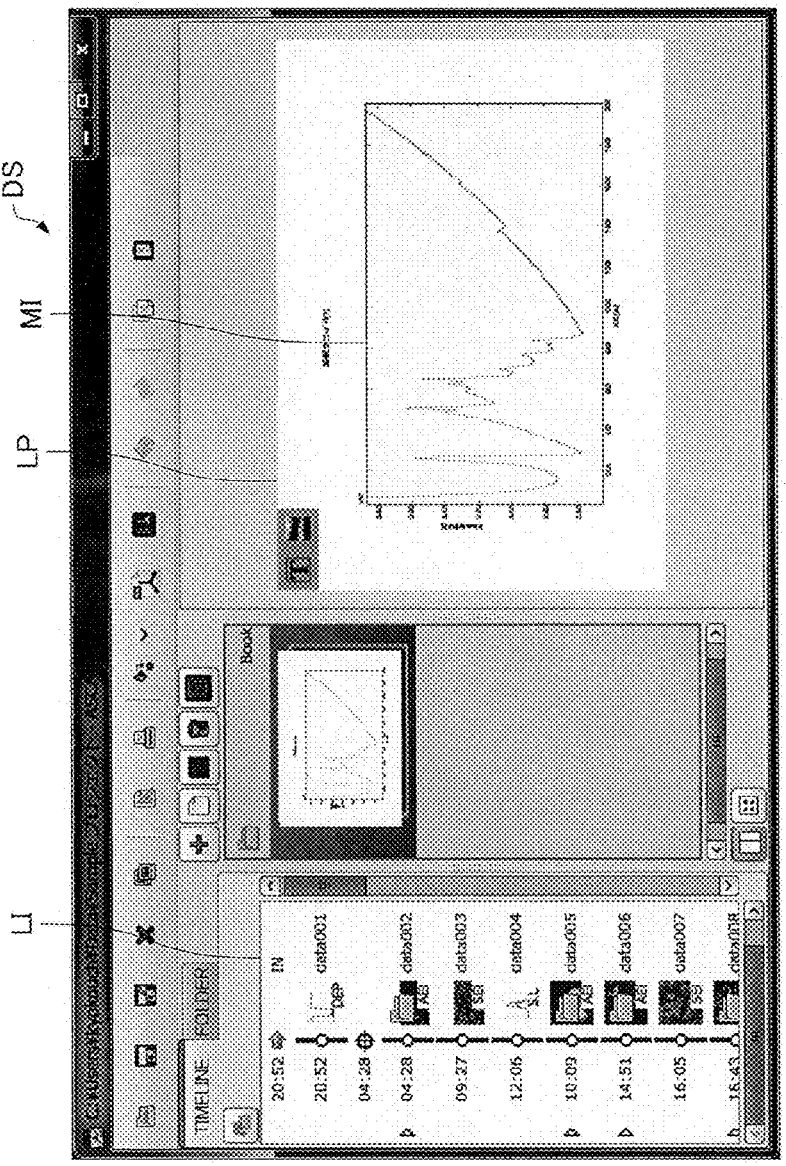
FIG. 2 illustrates an example of a display screen displayed on a display section.

FIG. 2 illustrates an example of the display screen (graphical user interface (GUI)) displayed on the display section 40. A log display area LI in which the history relating to the acquisition of the measurement data, the history relating to the analysis position, and the history relating to the analytical operation displayed in time series, is displayed in the left area of a display screen DS illustrated in FIG. 2, and a measurement result image MI generated based on the measurement data is displayed in the right area of the display screen DS.

The information processing device 10 stores the history relating to the acquisition of the measurement data, the history relating to the analysis position, and the history relating to the analytical operation in the storage section 50 as the log information 52 linked to the time information, and displays the time-series history illustrated in FIG. 2 within the log display area LI based on the log information 52. In this embodiment, position information about the specimen stage when the measurement data was acquired or the analytical operation was performed is recorded as the history relating to the analysis position. An operation that loads the specimen into the analyzer 1, information (e.g., etching depth, etching time, and ion gun conditions) about an operation that effects etching (sputtering) by applying ion beams, information (e.g., ON-OFF operation and ion gun conditions) about an operation that effects ion beam charge neutralization, and an that removes the specimen from the analyzer 1, are recorded as the history relating to the analytical operation. Note that information (e.g., a comparative image and drift during probe tracking) about a probe tracking operation or automatic probe tracking, and information about a maintenance operation (calibration) on the analyzer 1 may also be recorded as the history relating to the analytical operation. The degree of vacuum within the specimen chamber detected (monitored) when the measurement data was acquired may also be recorded as the log information 52.

FIG. 3 is a table illustrating an example of the log information 52. Log information 100 illustrated in FIG. 3 has a structure in which a history 130 (relating to the acquisition of the measurement data, the movement of the stage (change in the analysis position), an etching operation, and a neutralization operation) is linked to a time 120 (time information). Information 140 that represents the acquired measurement data is linked to the history relating to the acquisition of the measurement data. Identification information (ID) 110 is set to each history.

Figure 4:
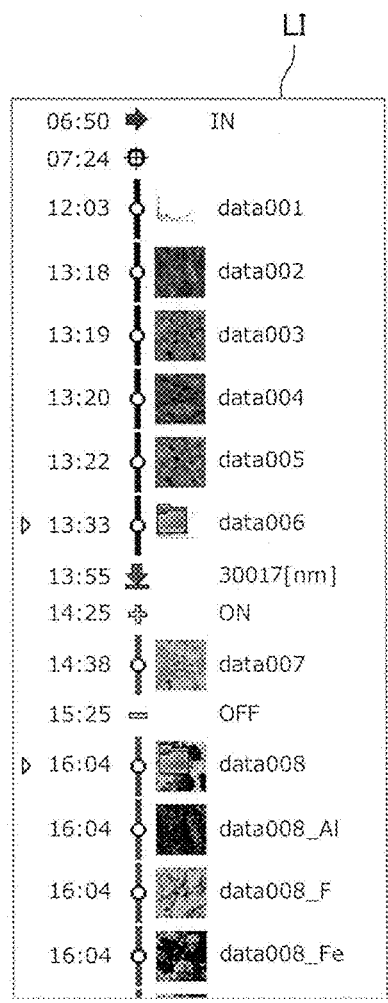
FIG. 4 illustrates an example of a log display area generated based on the log information illustrated in FIG. 3.

FIG. 4 illustrates an example of the log display area LI generated based on the log information 100 illustrated in FIG. 3. The time at which each event (i.e., the acquisition of the measurement data, the movement of the stage, or the analytical operation) occurred, and an icon that represents each event are displayed within the log display area LI. Regarding acquisition of the measurement data, a thumbnail of the measurement result image (spectrum, Auger image, or SEM image) generated based on the acquired measurement data is displayed, and the name of the measurement data is also displayed. The etching depth is displayed corresponding to the etching operation.

According to the log display area LI illustrated in FIG. 4, the specimen was loaded at time "06:50", the stage was moved (i.e., the analysis position was changed) at time "07:24", a spectrum "data001" was acquired at time "12:03", a plurality of SEM images "data002" to "data005" were acquired from time "13:18" to time "13:22", a plurality of spectra "data006" were acquired at time "13:33", an etching operation at a depth "30017 nm" was performed at time "13:55", a neutralization operation was started at time "14:25", an Auger image "data007" was acquired at time "14:38", the neutralization operation was stopped at time "15:25", and a plurality of Auger images "data008_A1", "data008_F", and "data008_Fe" were acquired at time "16:04".

Specifically, the pieces of measurement data "data001" to "data006" were acquired before the etching operation was performed, the pieces of measurement data "data007" to "data008_Fe" were acquired after the etching operation was performed, and the piece of measurement data "data007" was acquired while the neutralization operation was performed.

As stated above, since the history relating to the acquisition of the measurement data, the history relating to the analysis position, and the history relating to the analytical operation are displayed on the display screen in time series, this embodiment makes it possible to easily understand the situation before and after each piece of measurement data was acquired (i.e., the time and the situation when each piece of measurement data was measured). In particular, this embodiment makes it possible to provide information that is useful for a person (e.g., manager or client) other than the user (operator) who took part in the measurement to understand the grounds for the measurement data, and verify the validity of the measurement data.

In this embodiment, when the user has selected the desired measurement data displayed within the log display area LI, and performed a predetermined operation (e.g., double-click operation), a report that includes the measurement result image MI generated based on the selected measurement data is generated. In the example illustrated in FIG. 2, a report LP that includes the measurement result image MI is displayed (in an enlarged state) in the right area of the display screen DS, and thumbnails (list) of the generated report are displayed in the center area of the display screen DS.

Figure 5:
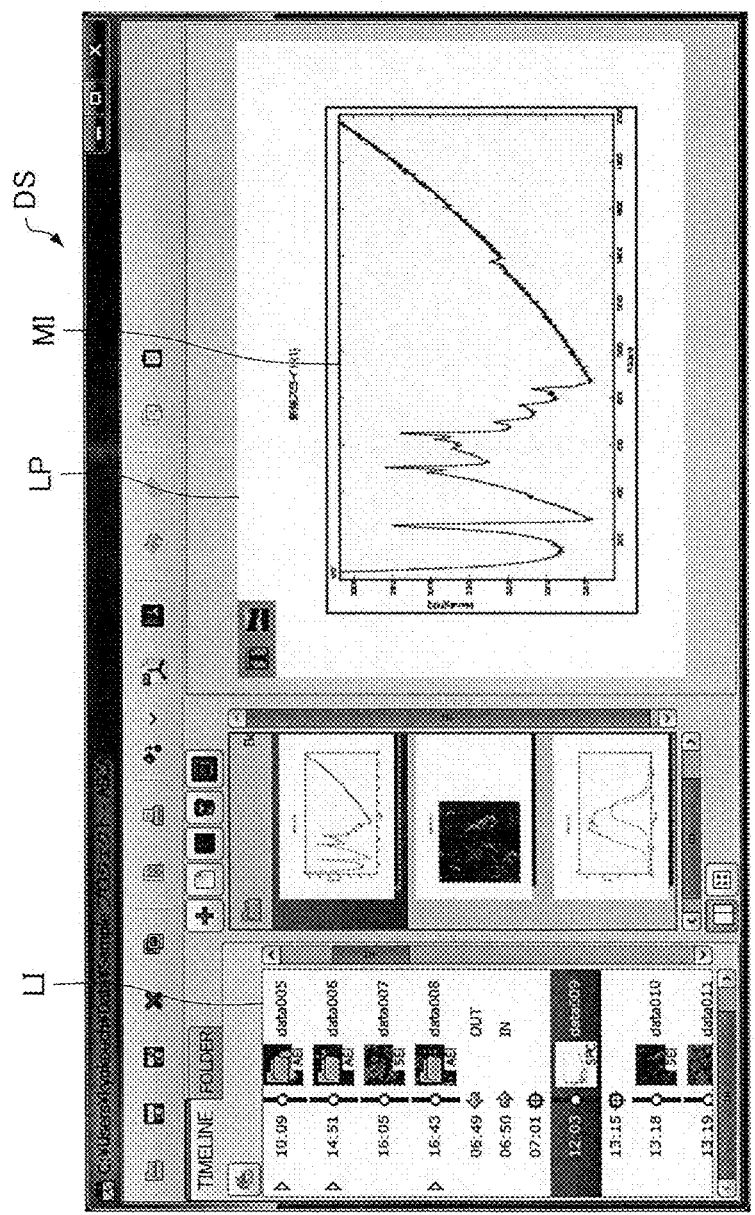
FIG. 5 illustrates an example of a display screen displayed on a display section.

When the user has performed an operation (e.g., click operation) that selects the measurement result image MI included in the report LP displayed in the right area of the display screen DS, a history that corresponds to the measurement data used to generate the selected measurement result image MI is displayed within the log display area LI so as to be specified. In the example illustrated in FIG. 5, since the measurement result image MI has been selected, a history that corresponds to the measurement data "data009" used to generate the measurement result image MI is displayed and highlighted (the colors of text and background are reversely displayed) within the log display area LI.

This makes it possible for the user to easily identify the history that corresponds to the measurement data used to generate the measurement result image included in the report LP within the log display area LI, and easily understand the situation before and after the measurement data was acquired. In particular, this makes it possible to provide information that is useful for a person (e.g., manager or client) other than the user who took part in the measurement to verify the validity of the measurement result image (and the measurement data used to generate the measurement result image) included in the report.

Note that information that represents the measurement data used to generate the measurement result image (corresponding to the information 140 included in the log information 100) is set (linked) to the measurement result image included in the report LP. When an operation input that selects the measurement result image included in the report LP has been performed, the display control section 22 performs a control process that specifies a history (i.e., the history identification information 110 included in the log information 100) that corresponds to the measurement data used to generate the measurement result image by referring to the log information based on the information set to the selected measurement result image, and highlights the specified history that corresponds to the measurement data within the log display area LI.

In this embodiment, the user can sort the history relating to the acquisition of the measurement data displayed within log display area LI in time series by the analysis position or the type of the analytical operation (using the analysis position or the type of the analytical operation as a key) by performing a predetermined operation so that the sorted history is displayed.

In the log display area LI illustrated in FIG. 6, the history relating to the acquisition of the measurement data is displayed in time series. According to the example illustrated in FIG. 6, the analysis position was moved to "FIELD OF VIEW 1" after the specimen was loaded, pieces of measurement data "data11" to "data13" were acquired in a state in which the analysis position was set to "FIELD OF VIEW 1", an etching operation was performed (depth: "100 nm"), pieces of measurement data "data14" to "data16" were acquired, an etching operation was performed (depth: "500 nm"), and pieces of measurement data "data17" to "data19" were acquired. The analysis position was then moved to "FIELD OF VIEW 2", pieces of measurement data "data21" to "data23" were acquired in a state in which the analysis position was set to "FIELD OF VIEW 2", an etching operation was performed (depth: "100 nm"), pieces of measurement data "data24" to "data26" were acquired, an etching operation was performed (depth: "500 nm"), and pieces of measurement data "data27" to "data29" were acquired.

Figure 7:
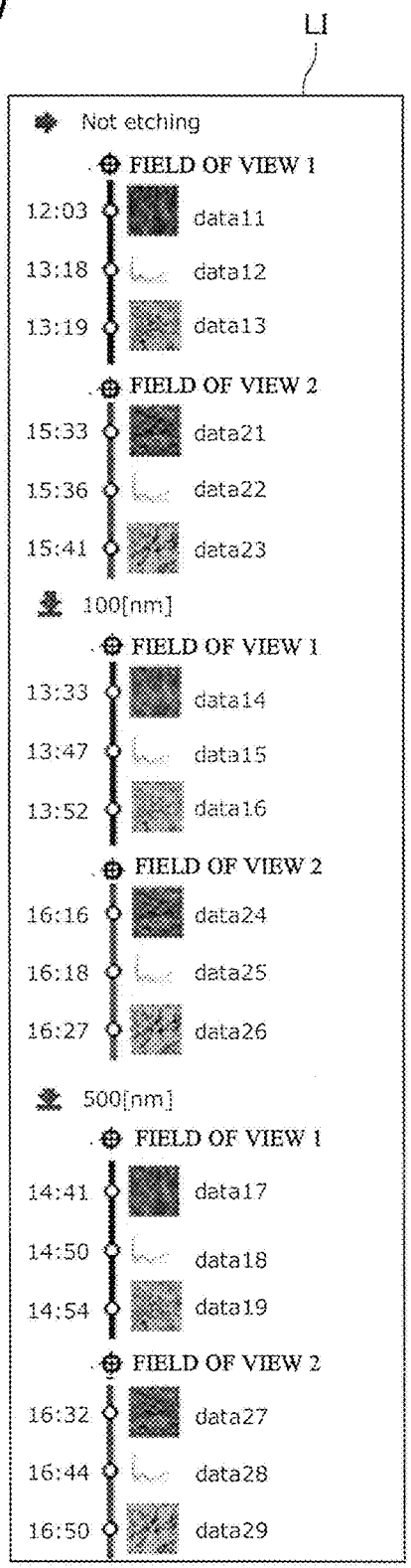
FIG. 7 illustrates a log display area when a history relating to the acquisition of measurement data is sorted by the type of operation.

When the user has performed an operation that instructs a sorting process based on the etching depth (i.e., the type of the analytical operation), the log display area LI is updated as illustrated in FIG. 7. In the log display area LI illustrated in FIG. 7, the history relating to the acquisition of the measurement data is displayed in a state in which the history is sorted by the etching depth (0 nm, 100 nm, 500 nm). Therefore, it is possible to easily understand that the pieces of measurement data "data11" to "data13" and "data21" to "data23" are measurement data at the surface of the specimen, the pieces of measurement data "data14" to "data16" and "data24" to "data26" are measurement data at a depth of 100 nm from the surface of the specimen, and the pieces of measurement data "data17" to "data19" and "data27" to "data29" are measurement data at a depth of 500 nm from the surface of the specimen.

As stated above, the user can easily understand the analysis position when each piece of measurement data was acquired, and the state of the specimen when each piece of measurement data was acquired by sorting the history relating to the acquisition of the measurement data by the analysis position or the type of the analytical operation, and displaying the sorted history. Therefore, it becomes possible to provide information useful for the user and the like.

Note that the history relating to the acquisition of the measurement data does not include information about the analysis position and the type of the analytical operation when each piece of measurement data was acquired. The display control section 22 specifies the analysis position and the type of the analytical operation when each piece of measurement data was acquired by tracing the history according to the time information (i.e., the time 120 included in the log information 100) referring to the log information 52, and performs the sorting process by the analysis position or the type of the analytical operation.

The invention is not limited to the above embodiments. Various modifications and variations may be made of the above embodiments. The invention includes configurations that are substantially the same as the configurations described in connection with the above embodiments (e.g., in function, method and effect, or objective and effect). The invention also includes a configuration in which an unsubstantial element among the elements described in connection with the above embodiments is replaced by another element. The invention also includes a configuration having the same effects as those of the configurations described in connection with the above embodiments, or a configuration capable of achieving the same object as those of the configurations described in connection with the above embodiments. The invention further includes a configuration obtained by adding known technology to the configurations described in connection with the above embodiments.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. An information processing device that processes measurement data acquired by an analyzer, the information processing device comprising:
   a storage section that stores a history relating to acquisition of the measurement data, a history relating to an analysis position within the analyzer, and a history relating to an operation that changes the state of the specimen consisting of surface treatment or etching step performed on a specimen using the analyzer as log information linked to time information; and a processing section comprising a computer, said processing section having a display control section programmed to perform a control process that displays the history relating to the acquisition of the measurement data, the history relating to the analysis position, and the history relating to the operation that changes the state of the specimen consisting of surface treatment or etching step within a log display area on a display screen in time series based on the log information, the display control section programmed to perform a control process that displays a measurement result image generated based on the measurement data on the display screen, and, when an operation input that selects one measurement result image among a plurality of the measurement result images has been performed, performing a control process that displays a history that corresponds to the measurement data used to generate the selected measurement result image within the log display area and highlights the measurement data log entry corresponding to the measurement result image displayed.

2. The information processing device as defined in claim 1, wherein the display control section is programmed to perform a control process that sorts the history relating to the acquisition of the measurement data by the analysis position or the type of the predetermined operation based on the log information, and displays the sorted history.

3. An information processing method that processes measurement data acquired by an analyzer, the information processing method comprising:

a storing step that stores a history relating to acquisition of the measurement data, a history relating to an analysis position within the analyzer, and a history relating to an operation that changes the state of the specimen consisting of surface treatment or etching step performed on a specimen using the analyzer in a storage section as log information linked to time information; and a display control step that performs a control process that displays the history relating to the acquisition of the measurement data, the history relating to the analysis position, and the history relating to the operation that changes the state of the specimen consisting of surface treatment or etching step within a log display area on a display screen in time series based on the log information, the display control step performing a control process that displays a measurement result image generated based on the measurement data on the display screen, and, when an operation input that selects one measurement result image among a plurality of the measurement result images has been performed, performing a control process that displays a history that corresponds to the measurement data used to generate the selected measurement result image within the log display area and highlights the measurement data log entry corresponding to the measurement result image displayed.

* * * * *